(12) United States Patent
Lightle

(10) Patent No.: US 6,364,843 B1
(45) Date of Patent: Apr. 2, 2002

(54) MEDICAL SANITATION SYSTEM

(76) Inventor: Roger Lightle, 309 St. Lucie La., Ft. Pierce, FL (US) 34946-1812

( * ) Notice: Subject to any disclaimer, the term of this patent is extended or adjusted under 35 U.S.C. 154(b) by 0 days.

(21) Appl. No.: 09/539,049

(22) Filed: Mar. 30, 2000

(51) Int. Cl.[7] .................................................. A61B 5/02
(52) U.S. Cl. .................... 600/490; 600/499; 606/202
(58) Field of Search ............................. 600/490, 499; 606/201–204; 604/307–308

(56) References Cited

U.S. PATENT DOCUMENTS

| | | | | |
|---|---|---|---|---|
| 4,548,249 A | * | 10/1985 | Slaughterbeck | 600/499 |
| 4,967,758 A | * | 11/1990 | Masciarotte | 600/499 X |
| 5,411,518 A | * | 5/1995 | Goldstein et al. | 600/499 |
| 5,513,643 A | * | 5/1996 | Suite | 600/499 |
| 5,620,001 A | * | 4/1997 | Byrd et al. | 600/499 |
| 5,651,368 A | * | 7/1997 | Napalitano et al. | 600/499 |
| 5,669,390 A | * | 9/1997 | McCormick et al. | 128/686 |
| 5,690,672 A | * | 11/1997 | Cohen | 606/203 |
| 5,797,851 A | * | 8/1998 | Byrd | 600/499 |

* cited by examiner

Primary Examiner—Robert L. Nasser

(57) ABSTRACT

A medical sanitation system for measuring blood pressure includes a cuff to be wrapped around the limb of a person. The cuff comprises a flexible strap with first and second ends which overlap for coupling. A first layer and a second layer of material define an internal compartment forming an inflatable bladder confined within the compartment. A first connector tube connects to a manually operated air supply pump and a second connector tube connects to a sphygmomanometer. A first fastening portion is secured at the first face of the strap and a second fastening portion is applied to the second face of the strap. A protective liner formed of a layer of absorbent material and a layer of liquid impermeable material prevents body fluids from contacting and contaminating the strap. The liner has a width greater than the width of the cuff. A fastener assembly secures the liner to the second face of the strap.

8 Claims, 4 Drawing Sheets

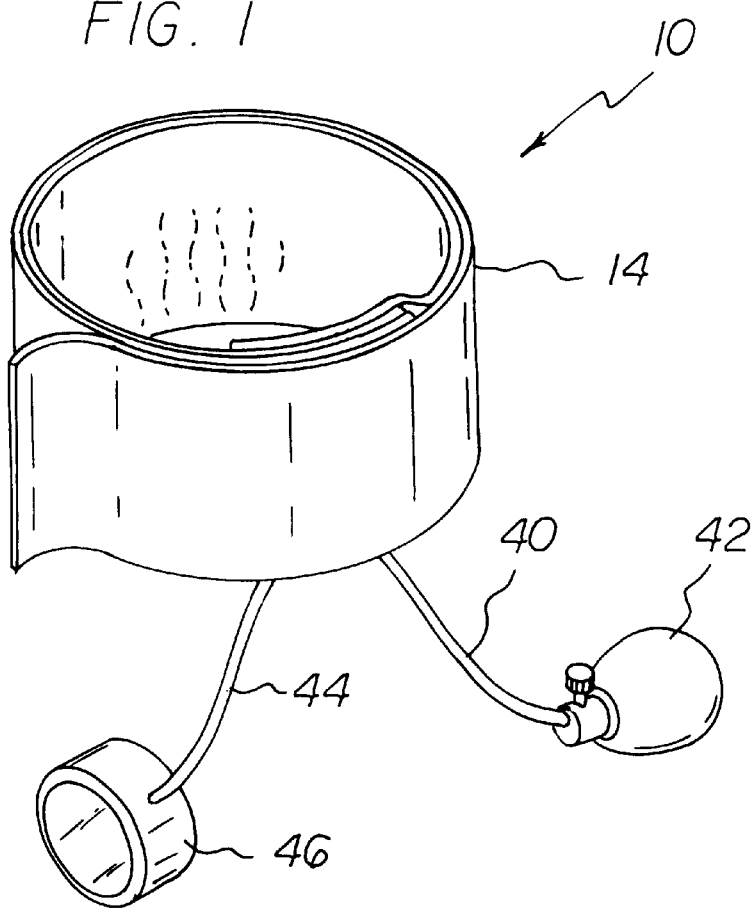
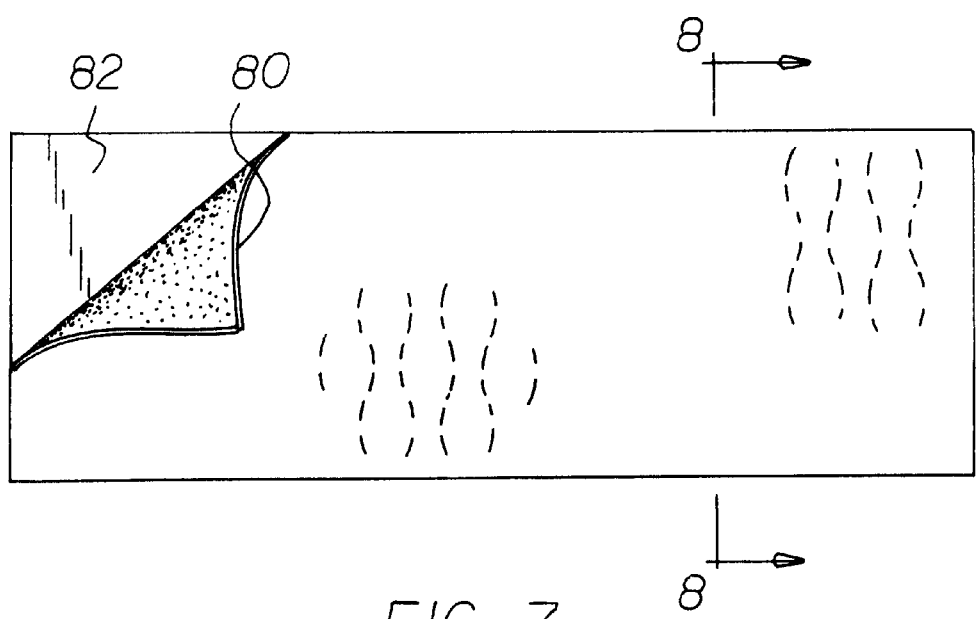

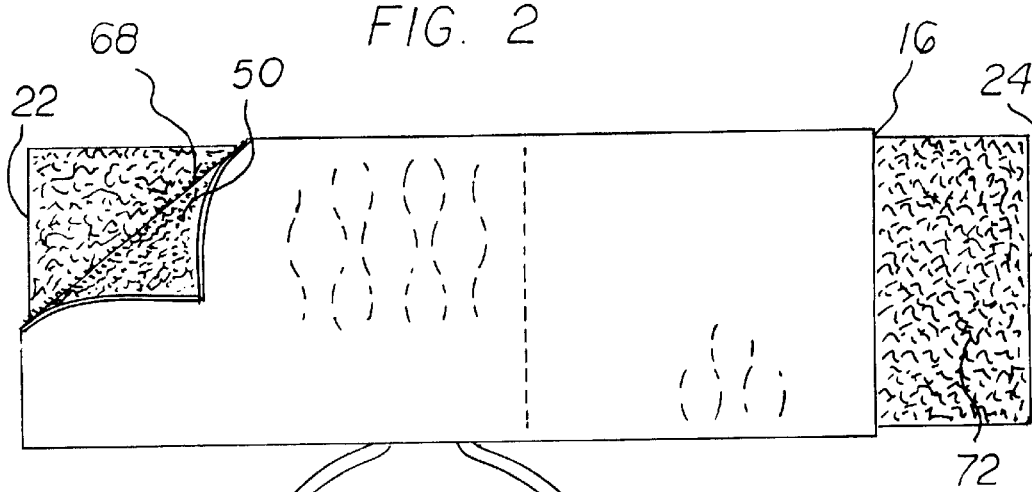
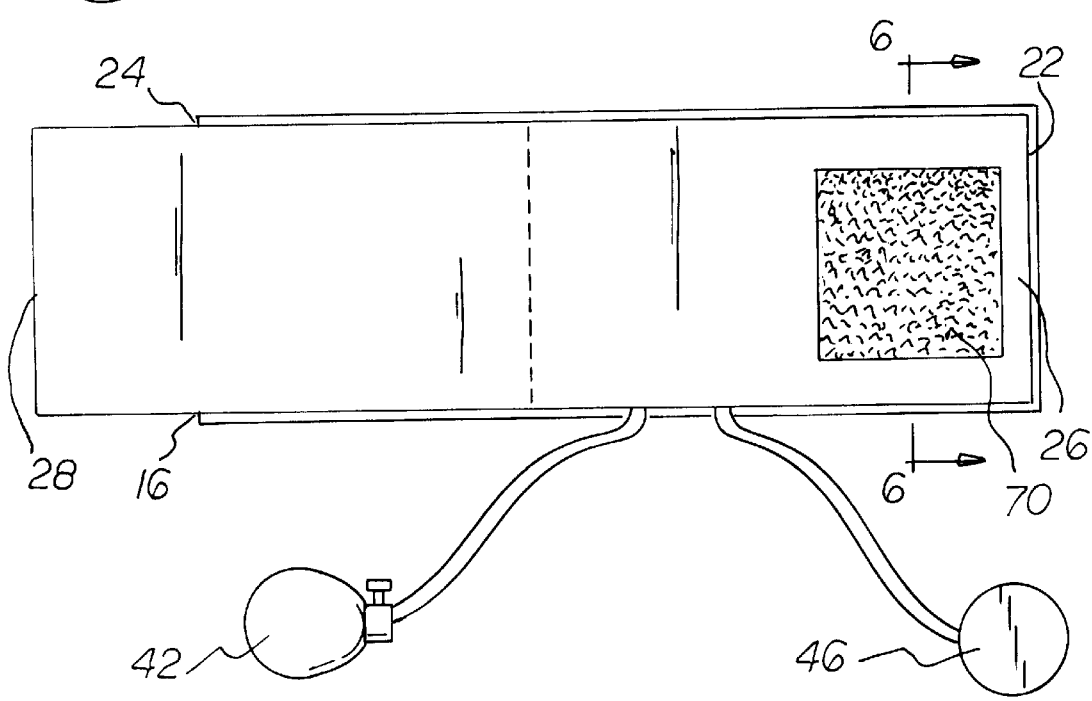

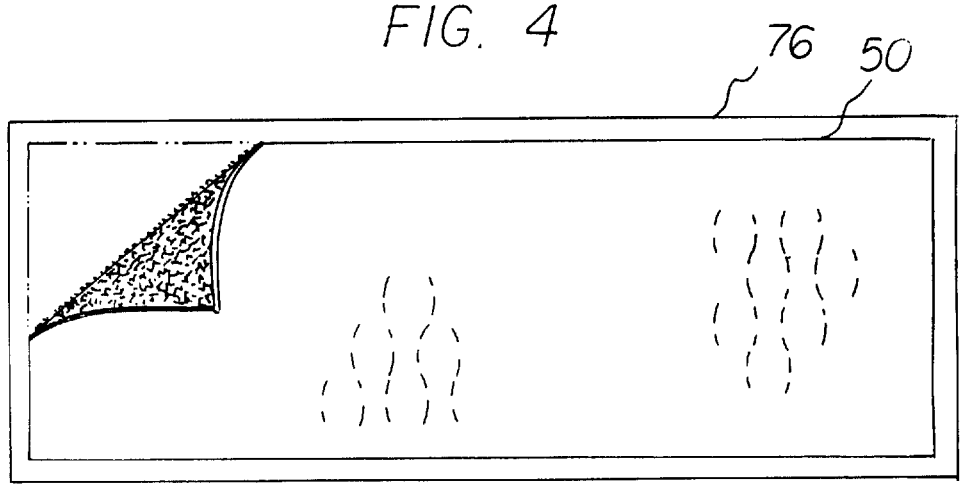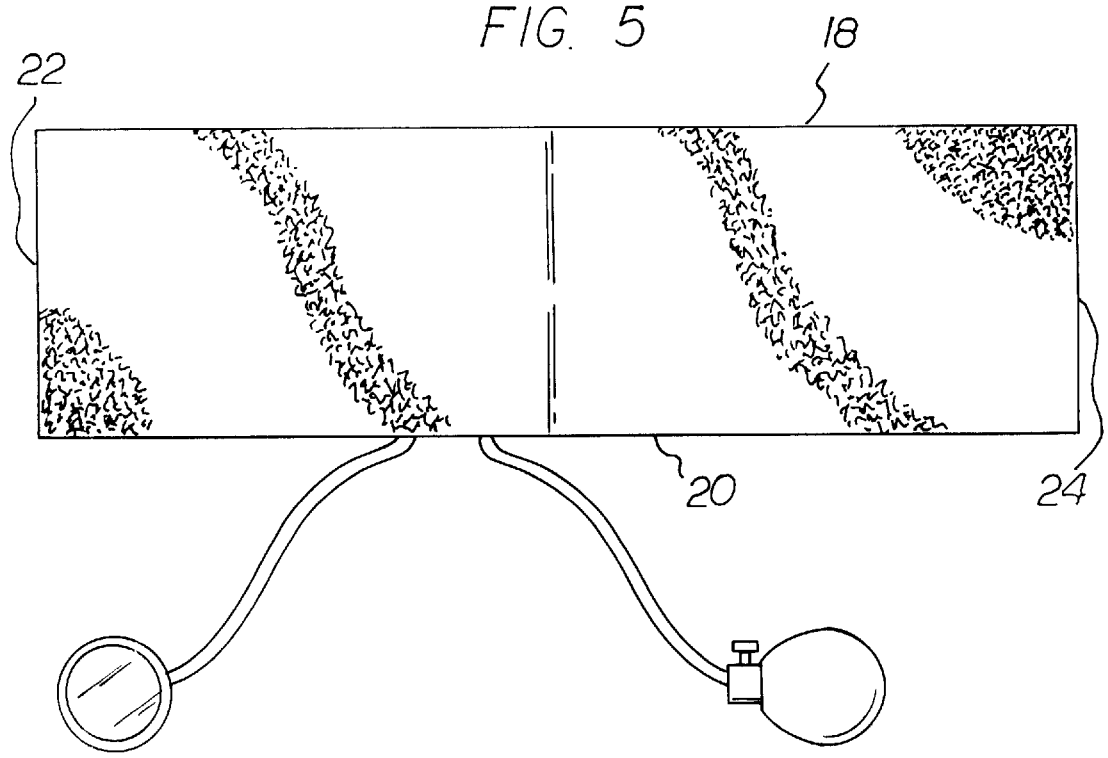

MEDICAL SANITATION SYSTEM

BACKGROUND OF THE INVENTION

1. Field of the Invention

The present invention relates to a medical sanitation system and more particularly pertains to a disposable cover removably secured to a blood pressure cuff capable of protecting the cuff from becoming contaminated and/or contaminating the patient.

2. Description of the Prior Art

The use of disposable covers for blood pressure cuffs is known in the prior art. More specifically, disposable covers of know designs and configurations previously devised and utilized for the purpose of protecting cuffs from becoming contaminated are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 5,228,448 to Byrd discloses a protective cover for a blood pressure cuff. U.S. Pat. No. 5,513,643 to Suite discloses a disposable protection wrap for use with a sphygmomanometer. Lastly, U.S. Pat. No. 5,620,002 to Byre et al discloses a universal blood pressure cuff cover.

While these devices fulfill their respective, particular objectives and requirements, the aforementioned patents do not describe a medical sanitation system that allows a disposable cover to be removably secured to a blood pressure cuff and for protecting the cuff from being contaminated or from contaminating the patient.

In this respect, the medical sanitation system according to the present invention substantially departs from the conventional concepts and designs of the prior art, and in doing so provides an apparatus primarily developed for the purpose of providing a disposable cover to be removably secured to a blood pressure cuff and for protecting the cuff from being contaminated or from contaminating the patient.

Therefore, it can be appreciated that there exists a continuing need for a new and improved medical sanitation system which can be used for protecting the cuff from removably securing a disposable liner to a blood pressure cuff and for protecting the cuff from becoming contaminated or from contaminating the patient. In this regard, the present invention substantially fulfills this need.

SUMMARY OF THE INVENTION

In view of the foregoing disadvantages inherent in the known types of disposable covers of known designs and configurations now present in the prior art, the present invention provides an improved medical sanitation system. As such, the general purpose of the present invention, which will be described subsequently in greater detail, is to provide a new and improved medical sanitation system and method which has all the advantages of the prior art and none of the disadvantages.

To attain this, the present invention essentially comprises a blood pressure cuff adapted to be wrapped around the arm of a person. The blood pressure cuff is formed of an elongated flexible strap in a rectangular configuration. The strap has long parallel upper and lower edges about 20½ inches in length and short parallel end edges about 5¾ inches in height. The strap has first and second ends so that the two ends overlap during operation and use. The strap is constituted by an interior layer of air impervious plastic material with an interior face and an exterior layer of air impervious elastomeric material with an exterior face. Defined within the interior layer and the exterior layer is a hollow internal compartment constituting an inflatable bladder. A first connector tube is provided and extends from the bladder for connecting to a manually operated air supply pump. A second connector tube is provided for connecting to a sphygmomanometer. A single use protective liner is provided. The liner is formed in a rectangular configuration with long parallel upper and lower edges about 18 inches in length and with short parallel end edges about 6 inches in height. The liner prevents body fluids from contacting and contaminating the strap between uses on successive patients. The liner is formed of a first layer of absorbent material, a middle layer of plastic material, and a hook shaped fastening layer to secure the liner to the interior face of the strap. The liner has a height greater than the height of the cuff for extending beyond the cuff when coupled to the cuff. A fastener assembly is next provided. The fastener assembly includes a square shaped hook fastening portion about 4 inches square secured at the exterior face of the strap adjacent to the second end of the cuff. The fastener assembly also include a loop fastening portion applied to the entire area of the interior face of the cuff. The loop fastening portion extends beyond the first end of the cuff by about 2 inches for coupling with the square shaped fastening portion. Lastly, a protective envelope is provided for the cover to ensure sanitation prior to use.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved medical sanitation system which has all of the advantages of the prior art disposable covers of known designs and configurations and none of the disadvantages.

It is another object of the present invention to provide a new and improved medical sanitation system which may be easily and efficiently manufactured and marketed.

It is further object of the present invention to provide a new and improved medical sanitation system which is of durable and reliable constructions.

An even further object of the present invention is to provide a new and improved medical sanitation system which is susceptible of a low cost of manufacture with regard to both materials and labor, and which accordingly is then susceptible of low prices of sale to the consuming public, thereby making such medical sanitation system economically available to the buying public.

Even still another object of the present invention is to provide a medical sanitation system for removably securing a disposable liner to a blood pressure cuff thereby protecting the cuff from becoming contaminated and/or contaminating the next following patent after a prior use.

Lastly, it is an object of the present invention to provide a new and improved A medical sanitation system for measuring blood pressure includes a cuff to be wrapped around the limb of a person. The cuff comprises a flexible strap with first and second ends which overlap for coupling. A first layer and a second layer of material define an internal compartment forming an inflatable bladder confined within the compartment. A first connector tube connects to a manually operated air supply pump and a second connector tube connects to a sphygmomanometer. A first fastening portion is secured at the first face of the strap and a second fastening portion is applied to the second face of the strap. A protective liner formed of a layer of absorbent material and a layer of liquid impermeable material prevents body fluids from contacting and contaminating the strap. The liner has a width greater than the width of the cuff. A fastener assembly secures the liner to the second face of the strap.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective illustration of the medical sanitation device in accordance with the principles of the present invention.

FIG. 2 is a perspective illustration of the blood pressure cuff with the disposable liner that embodies principles of the invention in a preferred form.

FIG. 3 is a plan view of the exterior face of the blood pressure cuff.

FIG. 4 is a front view of the disposable liner for the blood pressure cuff.

FIG. 5 is a plan view of the interior face of the blood pressure cuff.

FIG. 7 is a perspective view of the second embodiment of the invention.

The same reference numerals refer to the same parts throughout the various Figures.

DESCRIPTION OF THE PREFERRED EMBODIMENT

Figure 6:
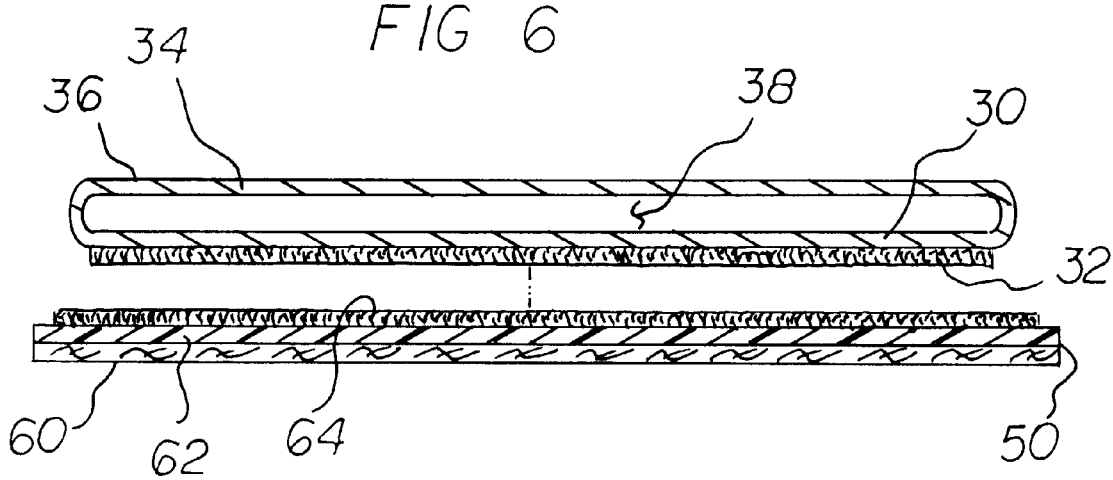
FIG. 6 is a cross sectional detail of the first preferred embodiment of the invention.
Figure 8:
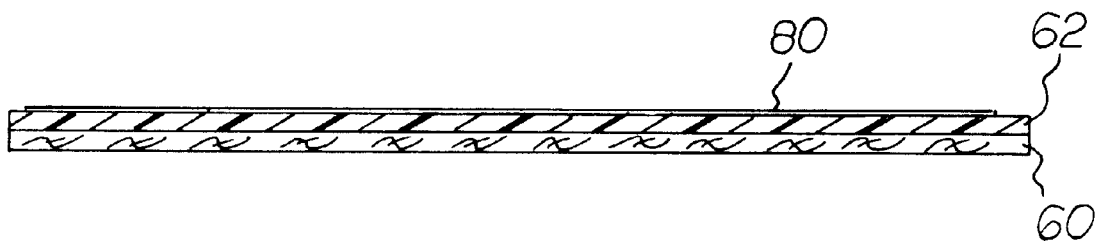
FIG. 8 is a cross sectional view of the disposable liner.

With reference now to the drawings, and in particular to FIG. 1 thereof, the preferred embodiment of the new and improved medical sanitation system embodying the principles and concepts of the present invention and generally designated by the reference numeral 10 will be described.

The present invention, the medical sanitation system 10 is comprised of a plurality of components. Such components in their broadest context include a cuff, a protective liner, and a fastener assembly. Such components are individually configured and correlated with respect to each other so as to attain the desired objective. The present invention essentially comprises a blood pressure cuff 14 adapted to be wrapped around the arm of a person. The blood pressure cuff is formed of an elongated flexible strap 16 in a rectangular configuration. The strap has long parallel upper and lower edges 18, 20 about 20½ inches in length and short parallel end edges 22, 24 about 5¾ inches in height. The strap has first and second ends 26, 28 so that the two ends overlap during operation and use. The strap is constituted by an interior layer 30 of air impervious plastic material with an interior face 32 and an exterior layer 34 of air impervious elastomeric material with an exterior face 36. Defined within the interior layer and the exterior layer is a hollow internal compartment 38 constituting an inflatable bladder. A first connector tube 40 is provided and extends from the bladder for connecting to a manually operated air supply pump 42. A second connector tube 44 is provided for connecting to a sphygmomanometer 46.

A single use protective liner 50 is provided. The liner is formed in a rectangular configuration with long parallel upper and lower edges 52, 54 about 18 inches in length and with short parallel end edges 56, 58 about 6 inches in height. The liner prevents body fluids from contacting and contaminating the strap between uses on successive patients. The liner is formed of a first layer 60 of absorbent material, a middle layer 62 of plastic material, and a hook shaped fastening layer 64 to secure the liner to the interior face of the strap. The liner has a height greater than the height of the cuff for extending beyond the cuff when coupled to the cuff.

A fastener assembly 68 is next provided. The fastener assembly includes a square shaped hook fastening portion 70 about 4 inches square secured at the exterior face of the strap adjacent to the second end of the cuff. The fastener assembly also include a loop fastening portion 72 applied to the entire area of the interior face of the cuff. The loop fastening portion extends beyond the first end of the cuff by about 2 inches for coupling with the square shaped fastening portion. Lastly, a protective envelope 76 is provided for the cover to ensure sanitation prior to use.

In an alternate embodiment the fastener assembly comprises an adhesive 80. The adhesive is of the type on catamenial shields attachable to panties. The adhesive is on the interior face of the liner of the cuff. The adhesive is adapted to be coupled to the interior face of the inner layer of the cuff prior to use and removed after a single use. A peel-off protective cover 82 for the adhesive is provided. The cover is adapted to be removed from the fastening assembly prior to use. Medical sanitation systems sphygmomanometer applications also apply for children's and large adult sphygmomanometers.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A medical sanitation system for measuring blood pressure in a limb of the body in a safe and convenient manner comprising, in combination:

a blood pressure cuff adapted to be wrapped around the arm of a person formed of an elongated flexible strap in a rectangular configuration with long parallel upper and lower edges about 20½ inches in length and with short parallel end edges about 5¾ inches in height having first and second ends so that the two ends overlap during operation and use, the strap being constituted by an interior layer of air impervious plastic material with an interior face and an exterior layer of air impervious elastomeric material with an exterior face to define a hollow internal compartment there within constituting an inflatable bladder formed by the layers and with a first connector tube extending from the bladder for connecting to a manually operated air supply pump and a second connector tube for connecting to a sphygmomanometer;

a single use protective liner in a rectangular configuration with long parallel upper and lower edges about 18 inches in length and with short parallel end edges about 6 inches in height for preventing body fluids from contacting and contaminating the strap between uses on successive patients, which comprises a first layer of absorbent material, a middle layer of plastic material, and a hook shaped fastening layer to secure the liner to the interior face of the strap, the liner having a height greater than the height of the cuff for extending there beyond when coupled to the cuff;

a fastener assembly including a square shaped hook fastening portion about 4 inches square secured at the exterior face of the strap of the cuff adjacent to the second end of the cuff and a loop fastening portion applied to the entire area of the interior face of the strap of the cuff, the cuff extending beyond the first end of the liner by about 2 inches for coupling with the square shaped fastening portion; and a protective envelope for the cover to ensure sanitation prior to use.

2. A medical sanitation system for measuring blood pressure comprising:

a cuff to be wrapped around the limb of a person comprising a flexible strap having first and second ends which overlap for coupling and having a first layer and a second layer of material to define an internal compartment forming an inflatable bladder confined within the compartment having a first connector tube for connecting to a manually operated air supply pump and a second connector tube for connecting to a sphygmomanometer, a first fastening portion secured at the first face of the strap and a second fastening portion applied to the second face of the strap, a protective liner for preventing body fluids from contacting and contaminating the strap having a width greater than the width of the cuff and a length less than the length of the cuff and formed of a layer of absorbent material and a layer of liquid impermeable material, and a fastener assembly to secure the liner to the second face of the strap.

3. The system as set forth in claim 2 wherein the flexible strap is in a rectangular configuration having a length of about 20½ inches and a height of about 5¾ inches.

4. The system as set forth in claim 2 wherein the protective liner is in a rectangular configuration having a length of about 18 inches and a height of about 6½ inches.

5. The system as set forth in claim 2 wherein the fastener assembly is in a square configuration having a length of about 3 inches and a width of about 3 inches and is secured at the exterior face of the strap about ½ inch from the edge.

6. The system as set forth in claim 2 wherein the fastener assembly comprises a hook and loop.

7. The system as set forth in claim 2 and further including a protective envelope for the cover to ensure sanitation prior to use.

8. The system as set forth in claim 2 wherein the fastener assembly comprises an adhesive of the type on catamenial shields attachable to panties on the interior face of the liner of the cuff adapted to be coupled to the interior face of the inner layer of the cuff prior to use and adapted to be removed after a single use and with a peel off protective cover for the adhesive and adapted to be removed from the fastening assembly prior to use.

* * * * *